(12) United States Patent
Logan et al.

(10) Patent No.: US 10,982,233 B2
(45) Date of Patent: Apr. 20, 2021

(54) METHOD OF PROCESSING ORGANIC MATTER

(71) Applicant: Eagle Green Energy II LLC, Prentiss, MS (US)

(72) Inventors: John William Logan, Prentiss, MS (US); Sumesh M Arora, Madison, MS (US); Richard L Vetter, Elgin, IL (US); Eric Francis Shafer, Magnolia, MS (US)

(73) Assignee: EAGLE GREEN ENERGY II LLC, Prentiss, MS (US)

( * ) Notice: Subject to any disclaimer, the term of this patent is extended or adjusted under 35 U.S.C. 154(b) by 37 days.

(21) Appl. No.: 15/806,115

(22) Filed: Nov. 7, 2017

(65) Prior Publication Data

US 2018/0127790 A1    May 10, 2018

Related U.S. Application Data

(60) Provisional application No. 62/418,494, filed on Nov. 7, 2016.

(51) Int. Cl.
*C12P 5/02* (2006.01)
*C10L 3/08* (2006.01)

(52) U.S. Cl.
CPC .................. *C12P 5/023* (2013.01); *C10L 3/08* (2013.01); *C10L 2290/26* (2013.01); *Y02E 50/30* (2013.01)

(58) Field of Classification Search
CPC ......... C12P 5/023; C10L 3/08; C10L 2290/26
See application file for complete search history.

(56) References Cited

U.S. PATENT DOCUMENTS

| | | | |
|---|---|---|---|
| 4,316,961 A * | 2/1982 | Klass | C12P 5/023 210/602 |
| 4,482,458 A | 11/1984 | Rovel et al. | |
| 5,096,579 A | 3/1992 | Jordan et al. | |
| 5,411,567 A | 5/1995 | Ueotani et al. | |
| 5,705,057 A | 1/1998 | Hoffa | |
| 5,746,919 A * | 5/1998 | Dague | C02F 3/286 210/603 |
| 5,942,116 A | 8/1999 | Clark et al. | |
| 6,254,775 B1 | 7/2001 | McElvaney | |
| 6,299,774 B1 | 10/2001 | Ainsworth et al. | |
| 6,521,129 B1 | 2/2003 | Stamper et al. | |
| 6,569,332 B2 | 5/2003 | Ainsworth et al. | |
| 7,186,339 B1 * | 3/2007 | Roos | A01C 3/023 210/603 |
| 7,785,467 B2 * | 8/2010 | Logan | B01F 3/04517 210/175 |
| 2002/0192809 A1 | 12/2002 | Lanting et al. | |
| 2010/0107872 A1 * | 5/2010 | Bethell | B01D 53/04 95/92 |

OTHER PUBLICATIONS

Collins et al. Optimal Loading Rates and Economic Analyses for Anaerobic Digestion of Poultry Waste. J. Air & Waste Manage. Assoc. 50:1037-1044 (Year: 2000).*

Renggaman et al. Underground anaerobic digester to solve the energy balance problem in temperate regions: A pilot study. Applied engineering in agriculture • Jul. 2015, vol. 31(4): 643-651 (Year: 2015).*

Jang et al. Microbial community structure in a thermophilic aerobic digester used as a sludge pretreatment process for the mesophilic anaerobic digestion and the enhancement of methane production. Bioresource Technology 145 (2013) 80-89 (Year: 2013).*

Miles, Dana M., et al. "On-Farm Resources and Renewable Energy in Broiler Chicken Production: Brinson Farms Case Study" International journal of Poultry Science 15 (2): 41-47, 2016.

* cited by examiner

*Primary Examiner* — Taeyoon Kim
(74) *Attorney, Agent, or Firm* — Nicholas J. Landau; Bradley Arant Boult Cummings LLP

(57) ABSTRACT

A process and system for treating biodegradable waste is described that utilizes serial thermophilic and mesophilic microbial digestion to product fuel gas and a stable solid product at high efficiencies.

41 Claims, 2 Drawing Sheets

METHOD OF PROCESSING ORGANIC MATTER

CROSS-REFERENCE TO RELATED APPLICATIONS

This application cites the priority of U.S. Provisional Application No. 62/418,494 filed on Nov. 7, 2016.

BACKGROUND

Field of the Disclosure

The field of the disclosure is biological waste treatment, specifically the anaerobic treatment of organic waste.

Background of the Art

Methane production by anaerobic digestion has been widely practiced, particularly with respect to digestion of sewage sludge organic waste. In recent times, the worldwide energy shortage has furthered consideration and improvement of such non-fossil sources of energy.

The production of methane gas by anaerobic digestion of various organic wastes has been known. There have been continuous efforts to improve methane yield resulting from anaerobic digestion. Most of the prior attempts to increase methane yield have been centered around anaerobic digestion as practiced in municipal waste treatment plants. Other attempts to improve the production rate and yield of methane by anaerobic digestion have related to improved anaerobic digestion by utilization of liberated enzymes of the biomass.

Due to constantly increasing demands for clean waste disposal options and fuel sources that do not liberate fossil carbon, there is a continuing need in the art for more efficient methods to convert organic waste to usable fuel.

SUMMARY

A process is disclosed for improved methane production from the serial thermophilic and mesophilic anaerobic digestion of mixtures of plant material and animal manure organic waste. It has been discovered that under certain conditions digestion of these mixed materials produces synergistic effects over the digestion of either material alone.

In a first aspect, a method of treating a mixed feedstock of organic waste and plant material is provided, the method comprising: digestion of the mixed feedstock under thermophilic conditions to create a primary digest product, followed by secondary digestion of the primary digest product under mesophilic conditions.

In a second aspect, a system for treating a mixed feedstock of organic waste and plant material is provided, the system comprising a primary digester configured to maintain the feedstock material under thermophilic and anaerobic conditions, and a second digester positioned to receive a primary digestion product from the primary digester and configured to maintain the primary digestion product under mesophilic and anaerobic conditions.

In a third aspect, a processed waste product is provided that is the product of the process above.

The above presents a simplified summary in order to provide a basic understanding of some aspects of the claimed subject matter. This summary is not an extensive overview. It is not intended to identify key or critical elements or to delineate the scope of the claimed subject matter. Its sole purpose is to present some concepts in a simplified form as a prelude to the more detailed description that is presented later

DETAILED DESCRIPTION

Figure 1:
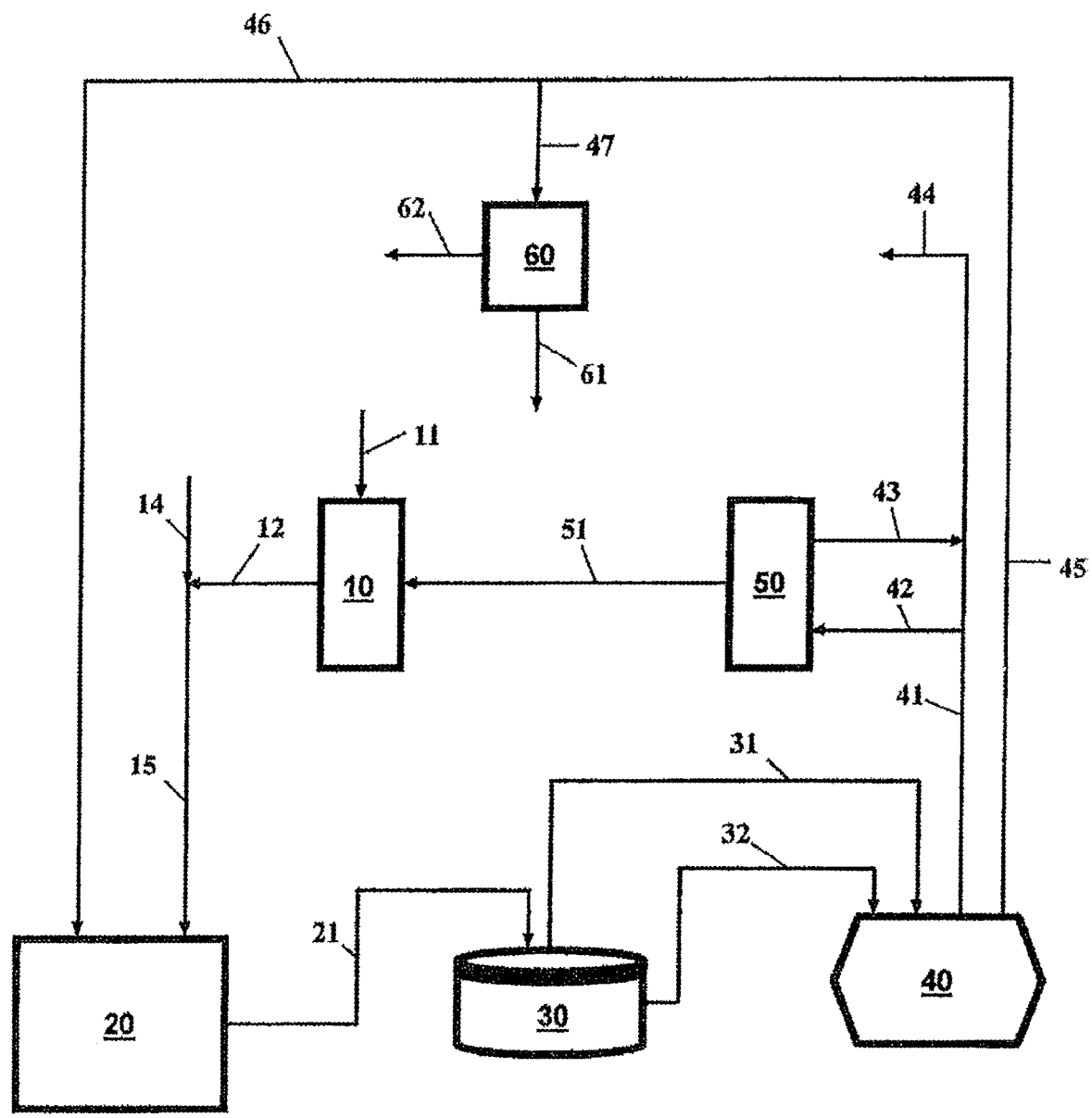
FIG. 1: A schematic of a first embodiment of the system.

Unless otherwise defined, all terms (including technical and scientific terms) used herein have the same meaning as commonly understood by one of ordinary skill in the art of this disclosure. It will be further understood that terms, such as those defined in commonly used dictionaries, should be interpreted as having a meaning that is consistent with their meaning in the context of the specification and should not be interpreted in an idealized or overly formal sense unless expressly so defined herein. Well known functions or constructions may not be described in detail for brevity or clarity.

The terms "about" and "approximately" shall generally mean an acceptable degree of error or variation for the quantity measured given the nature or precision of the measurements. Typical, exemplary degrees of error or variation are within 20 percent (%), preferably within 10%, and more preferably within 5% of a given value or range of values. Numerical quantities given in this description are approximate unless stated otherwise, meaning that the term "about" or "approximately" can be inferred when not expressly stated. Numerical quantities given in the claims are exact unless stated otherwise.

The terminology used herein is for the purpose of describing particular embodiments only and is not intended to be limiting. As used herein, the singular forms "a", "an" and "the" are intended to include the plural fat ns as well, unless the context clearly indicates otherwise.

The terms "first", "second", and the like are used herein to describe various features or elements, but these features or elements should not be limited by these terms. These terms are only used to distinguish one feature or element from another feature or element. Thus, a first feature or element discussed below could be termed a second feature or element, and similarly, a second feature or element discussed below could be termed a first feature or element without departing from the teachings of the present disclosure.

The term "consisting essentially of" means that, in addition to the recited elements, what is claimed may also contain other elements (steps, structures, ingredients, components, etc.) that do not adversely affect the operability of what is claimed for its intended purpose as stated in this disclosure. Importantly, this term excludes such other elements that adversely affect the operability of what is claimed for its intended purpose as stated in this disclosure, even if such other elements might enhance the operability of what is claimed for some other purpose.

Embodiments of the process provide production of methane gas in higher yields and higher rates by thermophilic and mesophilic anaerobic digestion combinations of a mixture of plant material and animal manure organic waste. The resulting methane yields and production rates are higher than those obtained by the sum from anaerobic digestion of the individual feed components. The plant material may be of terrestrial or aquatic origin. It is preferred that the plant material be a mixture of terrestrial and aquatic plant materials.

Retention times of the waste material at mesophilic and thermophilic temperatures may be in excess of five days. Washout is markedly less likely in embodiments of the process in which the retention time is at least 7 days, or more preferably at least 8 days. In some embodiments of the process the thermophilic retention time and the mesophilic retention time are independently selected from 5-50 days. In further embodiments of the process the thermophilic retention time and the mesophilic retention time are independently selected from 7-40 days. In further embodiments of the process the thermophilic retention time and the mesophilic retention time are independently selected from 8-40 days. In further embodiments of the process the thermophilic retention time and the mesophilic retention time are independently selected from 6-40 days. In still further embodiments of the process the thermophilic retention time and the mesophilic retention time are independently selected from 8-30 days. In still further embodiments of the process the thermophilic retention time and the mesophilic retention time are independently selected from 8-20 days. In a preferred embodiment of the process the thermophilic retention time and the mesophilic retention time are each about 11-16 days.

In some embodiments of the method the hydraulic retention time (HRT) and the solids retention time (SRT) vary relative to one another. For example, in some embodiments of the process the thermophilic digester both the SRT and the HRT are independently 12-15 days. In some embodiments of the process the mesophilic digester has an HRT of 5-10 days and an SRT of 15-40 days. The flow rates may be varied during the process in response to digester conditions and other processing requirements.

The term "plant material" as used in this description and the appended claims includes any of the organisms of the kingdom of Plantae which typically have cellulosic cell walls. The plant material useful in the feedstock may be fresh harvested or stored plant material, which is usually grown on farms for this purpose. It may be processed or it may be unprocessed chemically or physically; some embodiments of the plant material for the feedstock are unprocessed except for size reduction. The plant material may be from terrestrial plants, aquatic plants, or a combination thereof. Terrestrial plants can include warm season grasses, such as Bermuda grass and elephant grass; cool season grasses, such as Kentucky bluegrass and Merion bluegrass; reedy plants, such as bamboo, rice, cattails; herbaceous plants, such as kudzu and maize; deciduous trees, such as eucalyptus and poplar; and coniferous trees, such as white and red pine.

Exemplary aquatic plants include water hyacinth, duckweed, algae, sea kelp, and sargassum.

The term "organic waste" as used in this disclosure and the appended claims means all types of organic refuse including sewage sludge, animal waste, municipal waste, industrial waste, forestry waste, agricultural waste, and the like. Forestry waste and agricultural waste includes portions of plants after some physical or chemical treatment, whether or not including the entire plant. Examples include stumps from logging, sawdust, wood chips, corn stalks, corncob, and bagasse. If municipal solid waste or industrial solid waste are used, various methods for removal of undesired material such as glass, metals, plastics, stones, and the like, may be used prior to digestion.

In some embodiments of the process the plant material and organic waste are the principal feed materials, suitably in proportions of about 10 to about 90 weight percent on a dry solids basis of plant material and about 10 to about 90 weight percent on a dry solids basis of organic waste. In some embodiments of the process the combined plant material and organic waste is 20-100% w/w of the feedstock. Particularly preferred are mixtures in which the concentrations of plant material and organic poultry manure waste are independently selected from 30-70% w/w on a dry solids basis. Mixtures of individual organic wastes as described above may be used. Particularly preferred is poultry waste, including poultry feces, poultry bedding, and a combination thereof. Mixtures of individual plant materials as described above may be used. Particularly preferred are mixtures of terrestrial and aquatic plant materials. When a mixture of terrestrial plant material and aquatic plant material is used, it is suitable for the concentrations of each of organic poultry manure waste, terrestrial plant material and aquatic plant material in the feed mixture to be independently selected from 10-80% w/w on a dry solids basis, about 20-60% w/w on a dry solids basis of each of the components being preferred.

Methane production by anaerobic digestion according to the process using anaerobic digestion of a mixture of plant material and organic waste can be continued for long periods of time without addition of external nutrients. Methane production is stable over long periods of digestion. Plant materials, for example herbaceous plants such as giant reed, bamboo and grasses, and woody plants such as black alder, loblolly pine, eucalyptus and box elder which are recalcitrant to anaerobic digestion alone are readily digested using the process of this invention involving mixed plant material-organic waste feed. The effluent from the anaerobic digestion of a mixture of plant material and organic waste has a low concentration of soluble organics indicating low ultimate disposal cost and the feasibility of its recycle to the anaerobic digester with little or no treatment. The digested effluent, although diluted, can be dewatered directly by vacuum filtration to provide cake-solids content and cake yield comparable to that of filtered, digested sludge.

Some embodiments of the process result in higher yields and higher production rates than previously obtained by the separate anaerobic single stage digestion of organic poultry manure wastes and plant materials. Some embodiments of the process do not require the addition of external nutrients throughout the process. Some embodiments of the process result in digester effluent which can be easily dewatered. Still further embodiments of the process result in the digester effluent having a low concentration of soluble organics providing easy disposal and recycling to the digester with little or no treatment. Still further embodiments of the process provide methane production from plant material which is, by itself, recalcitrant to anaerobic digestion. Still further embodiments of the process are suitable for production of synthetic natural gas (SNG) by an anaerobic digestion process comprising anaerobic digestion of a mixture of plant material and organic poultry manure waste, thereby allowing better matching of organic waste and plant material feed supply for a better carbon nitrogen mixture for continuous year round operation. Still further embodiments of the process provide a hybrid plant material-organic waste methane production plant providing simultaneous energy recovery and animal waste nutrients stabilization Embodiments of the process may be carried out under conditions of temperature, both mesophilic (about 20-40° C.) and thermophilic (about 50-70° C.); retention times in excess of about 5 days and usually about 8 to 30 days, preferably about 11 to 16 days. Loading rates, pretreatment of feed, digester mixing and recycling may be varied as necessary.

The plant material and organic waste may be premixed prior to introduction into the digester or the individual feed materials may be separately introduced into the digester and mixed within the digester. Preferably the mixture of plant material and organic waste will be together in the active digestion zone. Feeding and associated wasting may be continuous or intermittent.

Methane-producing anaerobic systems utilizing organic acid forming (fermentative) bacteria and methanogenic organisms (such as those conventionally employed to produce methane from sewage sludge) can be employed during digestion. A review of the microbiology of anaerobic digestion is set forth in Anaerobic Digestion, I. The Microbiology of Anaerobic Digestion, D. F. Toerien and W. H. J. Hattingh, Water Research, Vol. 3, pages 385-416, Pergamum Press (1969). As set forth in that review, suitable non-methanogenic bacteria include species from genera including *Aerobacter, Aeromonas, Alcaligenes, Bacillus, Bacteroides, Clostridium, Escherichia, Klebsiella, Leptospira, Micrococcus, Neisseria, Paracolobactrum, Proteus, Pseudomonas, Rhodopseudomonas, Sarcina, Serratia, Streptococcus* and *Streptomyces*. Exemplary methane-producing organisms suitable for use in the process include specific species of the genera *Methanobacterium, Methanococcus*, and *Methanosarcina*; specific species including *Methanobacterium formicicum, Methanosarcina barkerii, Methanobacterium omelianskii, Methanococcus vannielii, Methanobacterium songenii, Methanosarcina methanol, Methanococcus mazei, Methanobacterium suboxydans*, and *Methanobacterium propionicum*. It is usually preferred to use mixed cultures to obtain the most complete fermentation action. Nutritional balance and pH adjustments may be made to the digester system to optimize methane production from the culture used.

Utilization of a mixture of plant material and organic poultry manure waste as a feed for the improved methane producing process of this invention is robust to problems of seasonable variables of materials for feed stock, such as plant material. The use of a mixture of plant materials helps to accommodate the seasonal variability of various species and geographic locations of farms for their production. Utilization of the mixed feedstock including organic waste provides simultaneous energy recovery in the form of methane and waste stabilization in an integrated process. The methane containing gas produced may be treated by methods known to the art to provide substitute natural gas (SNG).

Some embodiments of the process produce a synergistic yield of methane comprising multiple steps of digesting in an active mesophilic and thermophilic anaerobic digestion system with a mixture of plant material and organic poultry manure waste, and withdrawing methane-containing gas from the digestion system. The methane-containing gas may be a mixture of principally methane and carbon dioxide as produced by anaerobic digestion systems. Various means for increasing methane yield, gas quality and digestion kinetics involving feed pretreatment, residue post-treatment and recycling or advanced digestion modes may be used in the process.

Embodiments of the process produce a final gas product and a final slurry product. Some such embodiments of the process begin by admixing a biodegradable organic mass and a mass comprising water in a mixer unit to produce a paste product stream. Then the paste product stream is transferred into a primary thermophilic digester unit. The thermophilic digester unit may have a feed stream receiving structure suitable for flowing the paste product stream into the thermophilic digester unit. It may also have a gas product exit structure suitable for the flowing of a gas product stream from the thermophilic digester unit to an expandable storage system contained within the mesophilic digester (such as a bladder). The thermophilic digester unit may further have a slurry product exit structure suitable for the flowing of a slurry product stream from the thermophilic digester unit to the mesophilic digester. The thermophilic digester unit hosts a plurality of methanogenic organisms. Digestion in the thermophilic digester produces a first digestion gas. The process may involve the controlling of the temperature and the degree of mixture of the first digestion mass to produce an intermediate product gas stream and an intermediate slurry product stream.

The intermediate gas product stream may then flow from the thermophilic digester unit through the gas product exit structure to a mesophilic digester unit. The intermediate slurry product may flow from the thermophilic digester unit through a slurry product exit structure to the mesophilic digester unit, producing a second digestion mass in the mesophilic digester unit. A final gas product and a final slurry product may be achieved in the mesophilic digester by controlling the temperature and mixing rate of the contents of the second digestion mass is effective to produce the final gas product and the final slurry product.

The preferred biodegradable organic waste contains poultry manure, preferably broiler chicken manure, and preferably a content of 10-90% w/w poultry manure. Even more preferably the biodegradable organic mass further comprises a cellulose chicken house bedding mass. Before introduction into the thermophilic digester unit, the biodegradable organic mass may be comminuted to a paste mixture by admixing with water to arrive at a suitable digester feed consistency. In a preferred method, the mass comprising water is selected from the group consisting of: (1) a mass added to the biodegradable organic mass prior to the admixing, (2) a batch flow make-up water mass added directly to the mixer unit, and (3) a recycled mass from a portion of the final slurry product.

A heater unit may be employed, preferably operating off of gas generated in the digesters, which generates heated effluent mass to perform one or more of the steps of the group consisting of: (1) heating the paste product stream via direct addition of the heated effluent mass into the paste product stream, (2) performing by means of a heat exchanger unit the transfer of heat between the heated effluent mass and the paste product stream, and (3) performing by means of a heat exchanger unit the transfer of heat between the heated effluent mass and the first digester slurry mass.

Another preferred feature of the methods herein is use of a thermophilic digester unit which has means for removing the crust from the surface of the thermophilic digestion mass (decrusting). Exemplary embodiments of such means is the introduction of the feed streams over head of the liquid mass in the digester to impact any crust formations so as to break-up such crust and more preferably preventing full crust formation.

In the thermophilic digester unit, a preferred location of the heat exchanger unit is fixed by it being embedded on the external wall and floor of the thermophilic digester unit. More preferably, the heat exchanger unit is embedded below the floor of the thermophilic digester unit. Another preferred feature in the thermophilic digester is to configure the digester structure so that the slurry product exit structure is suitable for drawing the intermediate slurry product stream from the bottom region of the digestion slurry mass.

The operation of process flow through the thermophilic digester is preferably a continuous flow process. Such flow is an essentially continuous characteristic as those in the art will recognize that intermittent slow down or stoppage of flow can occur, but the operation should over the period of time involved be essentially continuous. Other embodiments of the process are batch processes. Accordingly, in a preferred mode of operation, the residence time of the thermophilic digester unit is about 18 days and the average temperature of the thermophilic digestion mass is about 50° C.

The mesophilic digester unit acts as a secondary digestion step and may also serve as a storage unit in keeping the gases, liquids and solids therein for potential continuous draw off or intermittent activity only. The thermophilic and mesophilic units can be characterized then as separately continuous operations or a combined continuous operation.

Superior thermal regulation can be achieved by locating some components of the system below ground level, essentially using the surrounding earth as insulation. Some embodiments of the system position of one or more units embedded in the ground sufficiently so that the level of liquidous content of one or more units is below ground level; such units may be selected from the group consisting of: (1) the mixer unit, (2) the thermophilic digester unit and (3) the mesophilic digester unit. The term "liquidous content" in this context means any fluid that is liquid, solid-in-liquid suspension, gas-in-liquid suspension, or liquid-in-solid suspension (i.e., it is not gaseous). Accordingly, in a preferred configuration the mesophilic digester unit is embedded in the ground sufficiently so that the level of liquidous content is below ground level and the mesophilic digester unit comprises a flexible top structure able to expand by force of the pressure of gaseous mass in the mesophilic digester unit. Materials for construction of such a unit are known in the art, such as rubber or polymeric sheets or the like.

The operation of the thermophilic digester unit preferably includes the step of performing by means of a heat exchanger unit the transfer of heat between the heated effluent mass and the digester mass by the use of multiple independent heating zones within the thermophilic unit as well as the mesophilic unit. The configuration of the mixing unit providing the feed stream into the thermophilic digester preferably should comprise at least one exterior pump with strong stirring power and a grinding blade. This applies particularly to the unit when it is embedded at least partly in the ground.

When the operation of the thermophilic digester unit is initiated, a preferred method is including the step of performing by means of a heat exchanger unit the transfer of heat between the heated effluent mass and the first digester slurry mass, such step being commenced when the level of the digester slurry mass has reached a minimal level. This minimal level is that which covers the heat transfer surfaces within the floor of the digester. This allows an earlier heating of the digester mass than typical operations in which the heating is delayed until higher elevated exterior heating surfaces, such as tubes rimming the exterior of the digester, are covered by the mass.

The biodegradable organic mass may comprise material derived from one or more types animal bedding. Conveniently this would be bedding from a broiler poultry operation. Optionally, the biodegradable organic mass further comprises one or more animal mass selected from the group of an animal excretion mass, an animal carcass, and a processed animal product, preferably broiler poultry waste. Unexpectedly, it has been discerned that the combination of the mass of various beddings and the waste of broiler poultry waste provides synergistic digestion compared to either mass independently digested.

Referring now to FIG. 1 there is depicted a process train 1 of unit operations for practicing one embodiment of the process. Within the process train 1 is a heating unit 10, a mixing unit 20, a thermophilic digester unit 30, a mesophilic digester unit 40, a separator unit 50, and a separator unit 60. Preferably, mixing unit 20 and mesophilic digester unit 40 are configured in the ground to a depth such that at least the liquid portion of the contents thereof is below ground. A glycol water stream is fed into process train 1 through line 11 (which may comprise ethylene glycol, propylene glycol, or a combination thereof). The purity of the water stream is within the discretion of the operator, but tap grade water is preferred of the closed loop heat exchange piping. The water stream passes through heating unit 10 to receive heat transfer from the combustion of products in heating unit 10. The heating unit 10 is a boiler unit configured for heat exchange between the combustion products and the water without mixing of the two masses. The water stream passes from heating unit 10 through line 12 for junction with line 14 with flow continuing through line 15. The water stream performs heat exchange at mixing unit 20 through heat coils around the exterior of the insulated walls (not shown), at thermophilic digestion unit 30 through heat coils within the floor and around the exterior of the insulated walls and at mesophilic digester unit 40 through heat coils below the liquid below ground.

In the embodiment shown in FIG. 1, a feed mass combination of poultry carcasses and poultry manure is fed into the process train 1 by introduction through line 14. This feed mass will combine with a water stream, if any, flowing from line 12. In a preferred embodiment, line 12 will have a valve control means to prevent back flow into line 12 from line 14. The mixture of feed mass and water stream then continues flowing through line 15 into mixing unit 20. Mixing unit 20 will receive a flow of recycled product mass through line 46 or tap grade water from line 11 for admixing with the feed mass received from line 15. Mixing and grinding occurs in mixing unit 20 to produce a paste product stream at a specific percent of mix which flows from mixing unit 20 through line 21 into thermophilic digester unit 30. Thermophilic digester unit 30 has within it a first digestion slurry mass which has been inoculated with a thermophilic methanogenic genera member capable of growing and producing methane in the environs of the digestion slurry mass within thermophilic digester unit 30. Accordingly, thermophilic digester unit 30 has within it the aforementioned digestion slurry mass and a mass of digestion gaseous product in a head space over the slurry mass. Through line 31 flows an intermediate gas product stream from the head space into mesophilic digester unit 40. Through line 32 flows an intermediate slurry product stream from the overflow digestion slurry mass into mesophilic digester unit 40 containing one or more types of mesophilic methanogenic archaebacterium. A final combined gaseous product flows from mesophilic digester unit 40 through line 41. The gas product is taken off through line 42 for treatment in separator unit 50 in which a methane product is separated and transferred through line 51 for use as a combustion fuel in heating unit 10. The balance of the separated gaseous product fed into separator unit 50 will be recovered as an independent product gas or returned for flow through line 43 through line 44 for recovery as a final product. A final slurry product flows from mesophilic digester unit 40 through line 45. A first portion of the liquid slurry product may be taken off through line 46 for recycle to mixing unit 20 as previously alluded. A second portion continues through line 47 for treatment in separator unit 60 in which a separation into a final liquidous product is recovered through line 61 and a final solid product is recovered through line 62. When gaseous products from separator unit 50 are used for cogeneration of electricity, heat captured through engine exhaust and water cooling is captured and flows to heating unit 10 (not shown in FIG. 1).

Figure 2:
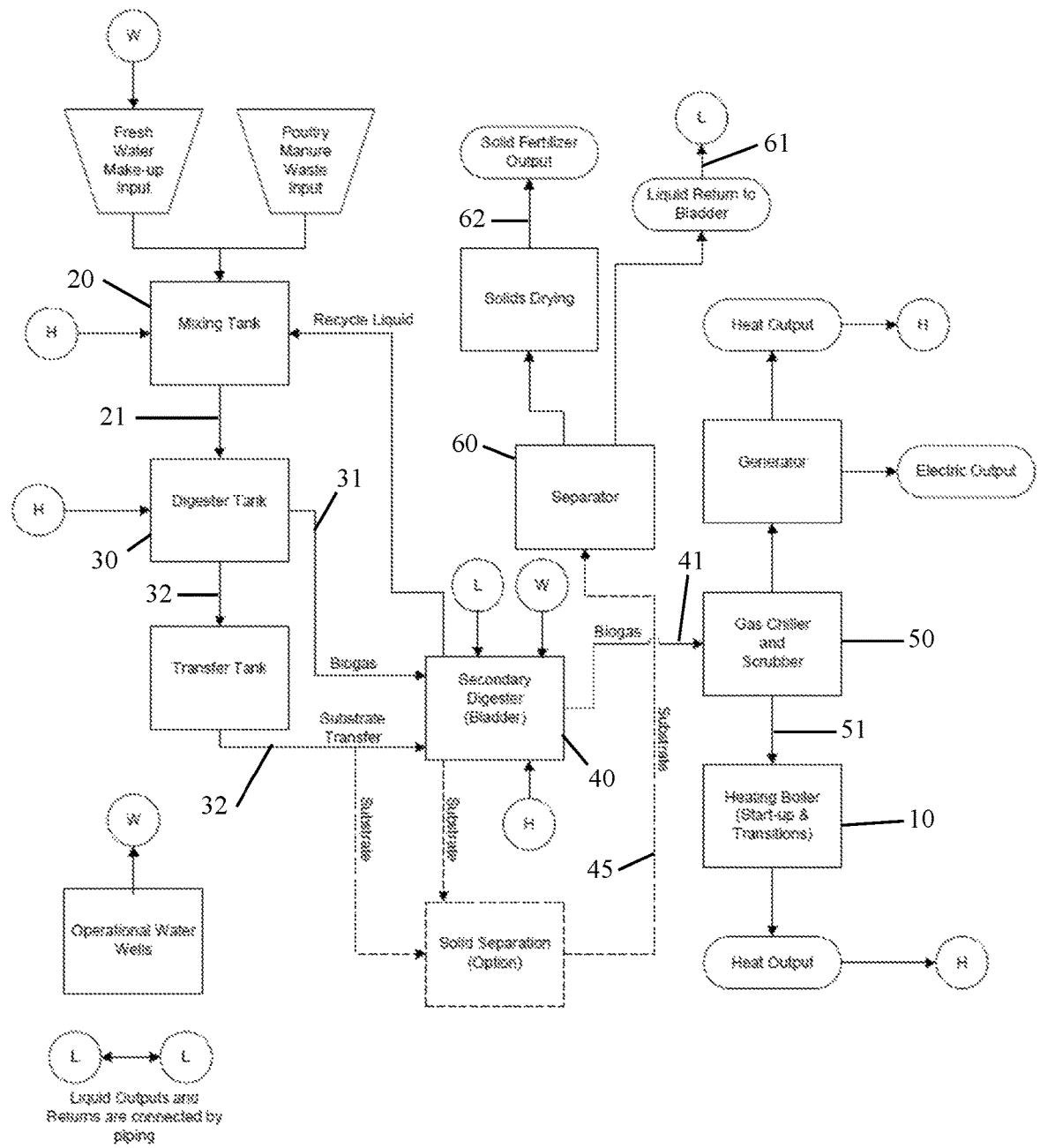
FIG. 2: A schematic of a second embodiment of the system.

A further embodiment of the system is shown in FIG. 2.

It is to be understood that any given elements of the disclosed embodiments of the invention may be embodied in a single structure, a single step, a single substance, or the like. Similarly, a given element of the disclosed embodiment may be embodied in multiple structures, steps, substances, or the like.

The foregoing description illustrates and describes the processes, machines, manufactures, compositions of matter, and other teachings of the present disclosure. Additionally, the disclosure shows and describes only certain embodiments of the processes, machines, manufactures, compositions of matter, and other teachings disclosed, but, as mentioned above, it is to be understood that the teachings of the present disclosure are capable of use in various other combinations, modifications, and environments and is capable of changes or modifications within the scope of the teachings as expressed herein, commensurate with the skill and/or knowledge of a person having ordinary skill in the relevant art. The embodiments described hereinabove are further intended to explain certain best modes known of practicing the processes, machines, manufactures, compositions of matter, and other teachings of the present disclosure and to enable others skilled in the art to utilize the teachings of the present disclosure in such, or other, embodiments and with the various modifications required by the particular applications or uses. Accordingly, the processes, machines, manufactures, compositions of matter, and other teachings of the present disclosure are not intended to limit the exact embodiments and examples disclosed herein. Any section headings herein are provided only for consistency with the suggestions of 37 C.F.R. § 1.77 or otherwise to provide organizational queues. These headings shall not limit or characterize the invention(s) set forth herein.

What is claimed is:

1. A method for processing a biodegradable organic mass to produce a final gas product and a final slurry product, the processing comprising:
   (a) inoculating a thermophilic digester unit with a culture comprising a population of thermophilic methanogenic organisms;
   (b) introducing the biodegradable organic mass into the thermophilic digester unit, wherein the thermophilic digester unit contains the population of thermophilic methanogenic organisms, wherein a first digestion slurry mass and a first digestion gas mass from the biodegradable organic mass is produced, and wherein the thermophilic digester unit is maintained at a thermophilic temperature, pH, and mixing rate permissive to the generation of methane by the population of thermophilic methanogenic organisms;
   (c) transporting the first digestion gas mass from the thermophilic digester unit to a mesophilic digester unit maintained at a mesophilic temperature;
   (d) transporting the first digestion slurry mass from the thermophilic digester unit to the mesophilic digester unit; and
   (e) producing a final gas product and a final slurry product at least in part from the first digestion gas mass and the first digestion slurry mass in the mesophilic digester unit.

2. The method of claim 1 wherein the biodegradable organic mass comprises poultry excrement.

3. The method of claim 2 wherein the biodegradable organic mass comprises a cellulose bedding mass.

4. The method of claim 2 comprising reducing the biodegradable organic mass in size and blending the biodegradable organic mass with liquid a to achieve a predetermined level of solids before the introducing of the biodegradable organic mass into the thermophilic digester unit.

5. The method of claim 4, wherein the liquid is recycled a liquid from a portion of the final slurry product.

6. The method of claim 1 wherein the thermophilic digester unit further comprises a decrusting unit positioned to decrust a surface of the first digestion slurry mass.

7. The method of claim 1 wherein a slurry product exit structure is provided in the thermophilic digester, and is configured for drawing the first digestion slurry mass from a bottom region of the thermophilic digester.

8. The method of claim 1 wherein the processing is essentially a continuous flow processing.

9. The method of claim 8 wherein the thermophilic digester unit comprises an average solid retention time of about 18 days and the average temperature of the first slurry digestion mass is about 70° C.

10. The method of claim 1 wherein one or more units selected from the group consisting of (1) a mixer unit, (2) the thermophilic digester unit and (3) the mesophilic digester unit; are embedded in the ground sufficiently so that the level of liquidous content of the unit(s) is below ground level.

11. The method of claim 9 wherein the mesophilic digester unit comprises a flexible top structure configured to expand by gas pressure in the mesophilic digester unit.

12. The method of claim 1 wherein the mesophilic digester unit comprises multiple independent heating zones.

13. The method of claim 1 wherein the thermophilic digester unit comprises an exterior pump and a grinding blade.

14. The method of claim 1 wherein the biodegradable organic mass comprises poultry carcasses.

15. The method of claim 1 wherein the biodegradable organic mass comprises a portion of animal bedding.

16. The method of claim 1 wherein the biodegradable organic mass further comprises one or more animal mass selected from the group consisting of an animal excretion mass, an animal carcass, a processed animal product, and combinations thereof.

17. The method of claim 15 wherein the animal excretion mass is broiler poultry excrement.

18. The method of claim 1 wherein the thermophilic methanogens comprise a thermophilic methanogenic genus selected from the group consisting of: *Methanosarcina, Methanosaeta*, and combinations thereof.

19. A process for producing a fuel gas from an organic matter feedstock comprising at least 10% animal waste, the process comprising:
   (a) introducing the organic matter feedstock to a thermophilic digester maintained under thermophilic and anaerobic conditions for an average solids retention time of at least 4 days, to produce a first gas product and a first slurry product; and (b) transferring at least a portion of the first gas product and at least a portion of the first slurry product to a mesophilic bladder digester maintained under mesophilic and anaerobic conditions for an average solids retention time of at least 4 days, to produce a second gas product and a second slurry product.

20. The process of claim 19, wherein the thermophilic digester contains a population of thermophilic methanogenic organisms.

21. The process of claim 19, wherein the mesophilic bladder digester contains a population of mesophilic methanogenic organisms.

22. The process of claim 19, wherein the thermophilic digester contains a population of thermophilic fermentative bacteria.

23. The process of claim 19, wherein the mesophilic bladder digester contains a population of mesophilic fermentative bacteria.

24. The process of claim 19, wherein all of the first gas product is transferred to the mesophilic bladder digester.

25. The process of claim 19, wherein the organic matter feedstock is at least 20% w/w of animal waste and plant matter.

26. The process of claim 25, wherein the concentration of combined animal waste and plant matter in the organic matter feedstock is least at 30%, 40%, 50%, 60%, 70%, 80%, 90%, 95%, 99%, or 100% w/w.

27. The process of claim 19, wherein the animal waste comprises one or more of: animal excrement, animal bedding material, animal body parts, animal feathers, and animal hair.

28. The process of claim 19, wherein the animal waste is at least 50% w/w of poultry excrement.

29. The process of claim 19, comprising dewatering the second slurry product to generate a final solid product.

30. The process of claim 19, comprising purifying a fuel gas from the second gas product.

31. The process of claim 19, comprising purifying a fuel gas from the second gas product and combusting the fuel gas to generate one or both of heat or electricity.

32. The process of claim 19, comprising purifying a fuel gas from the second gas product and storing the fuel gas as a compressed gas.

33. The process of claim 19, comprising mixing the animal waste with a volume of mixing water prior to the step of introducing the organic matter feedstock to the thermophilic digester.

34. The process of claim 19, wherein the average solids retention time in the thermophilic digester is selected from the group consisting of: at least 7 days, at least 8 days, 8-20 days, and 11-16 days.

35. The process of claim 19, wherein the average solids retention time in the mesophilic digester is selected from the group consisting of: at least 7 days, at least 8 days, 7-50 days, 7-40 days, 8-50 days, 8-40 days, 5-50 days, 6-40 days, and 8-30 days.

36. The method of claim 19, wherein the average solids retention time in the thermophilic digester is about 18 days and the average temperature of the thermophilic digester is about 50 to about 70° C.

37. The process of claim 19, wherein at least one of the thermophilic digester or the second mesophilic bladder digester is at least partially below ground level.

38. The process of claim 19, wherein at least a portion of the second slurry product is recycled for use as feedstock.

39. The process of claim 19, wherein the average solids retention time in the thermophilic digester is less than the average solids retention time in the mesophilic bladder digester.

40. The process of claim 19, wherein the average solids retention time in the thermophilic digester is up to about 18 days and the average solids retention time in the mesophilic bladder digester is up to about 40 days.

41. The process of claim 19, wherein the mesophilic bladder digester comprises a flexible top structure configured to expand by gas pressure in the mesophilic bladder digester.

\* \* \* \* \*